US 006627246B2

(12) United States Patent
Mehta et al.

(10) Patent No.: US 6,627,246 B2
(45) Date of Patent: Sep. 30, 2003

(54) PROCESS FOR COATING STENTS AND OTHER MEDICAL DEVICES USING SUPER-CRITICAL CARBON DIOXIDE

(75) Inventors: Deepak B. Mehta, Warren, NJ (US); Michael Corbo, Flemington, NJ (US)

(73) Assignee: Ortho-McNeil Pharmaceutical, Inc., Raritan, NJ (US)

( * ) Notice: Subject to any disclaimer, the term of this patent is extended or adjusted under 35 U.S.C. 154(b) by 0 days.

(21) Appl. No.: 09/836,161

(22) Filed: Apr. 17, 2001

(65) Prior Publication Data

US 2002/0051845 A1 May 2, 2002

Related U.S. Application Data

(60) Provisional application No. 60/204,991, filed on May 16, 2000.

(51) Int. Cl.[7] .................. A61L 27/00; A61L 27/28; A61L 27/54; B05D 1/02
(52) U.S. Cl. ............ 427/2.1; 427/2.14; 427/2.24; 427/2.25; 427/2.26; 427/2.28; 427/2.3; 427/2.31; 427/244; 427/407.1; 427/409; 427/421
(58) Field of Search ................ 427/2.1, 2.14, 427/2.24, 2.25, 2.26, 2.28, 2.3, 2.314, 244, 407.1, 409, 421

(56) References Cited

U.S. PATENT DOCUMENTS

| 4,737,384 | A | | 4/1988 | Murthy et al. |
| 5,340,614 | A | | 8/1994 | Perman et al. |
| 5,639,441 | A | * | 6/1997 | Sievers et al. ......... 128/200.23 |
| 5,916,585 | A | * | 6/1999 | Cook et al. .................. 424/426 |
| 6,350,786 | B1 | * | 2/2002 | Albano et al. ............... 424/465 |

FOREIGN PATENT DOCUMENTS

| DE | 42 02 320 A | | 8/1993 | |
| EP | 0 405 284 A | | 1/1991 | |
| EP | 0 405 284 A2 | * | 1/1991 | ........... A61L/29/00 |
| JP | 11 255925 A | | 9/1999 | |
| WO | WO 91/09079 A1 | | 6/1991 | |
| WO | WO 99/10985 A1 | | 4/1999 | |

OTHER PUBLICATIONS

Benken R. et al; "Impregnating substrate by contact with supercritical fluid contg. Impregnant—followed by conversion of fluid to subcritical state", English Abstract of German Patent No. DE 4202320 A; Aug. 5, 1993; Dialog File No. 351 Accession No. 9618753; Derwent World Patents Index; 2003 Derwent Information Ltd.

Tsuneo, H. ; Modification of Medical Polymer and Polymer Base Material for Medical Purpose; English Abstract of Japanese Publication No. JP 11–255925A; Sep. 21, 1999; Dialog File No. 347 Accession No. 6314327; 2003 Japan Patent Information Organization.

* cited by examiner

Primary Examiner—Shrive P. Beck
Assistant Examiner—Jennifer Kolb Michener

(57) ABSTRACT

This invention provides an improved process for coating medical and surgical devices and the like using super-critical fluids.

7 Claims, 6 Drawing Sheets

CAP:GLY = caprolactone:glycolide co-polymer

PROCESS FOR COATING STENTS AND OTHER MEDICAL DEVICES USING SUPER-CRITICAL CARBON DIOXIDE

This application claims benefit of provisional application Ser. No. 60/204,991 filed May 16, 2000 (now abandoned).

FIELD OF THE INVENTION

The invention relates generally to a process for coating medical devices, particularly surgical devices such as stents. More specifically this invention relates to an improved process for coating stents and the like using super-critical carbon dioxide.

BACKGROUND OF THE INVENTION

Stents, which are generally open tubular structures, have become increasingly important in medical procedures to restore the function of body lumens. Stents are now commonly used in translumenial procedures such as angioplasty to restore an adequate blood flow to the heart. However, stents may stimulate foreign body reactions that result in thrombosis or restenosis. To avoid these complications a variety of polymeric stent coatings and compositions have been proposed in the literature both to reduce the incidence of these or other complications or by delivering therapeutic compounds such as thrombolytics to the lumen to prevent thrombosis or restenosis. For example stents coated with polymers containing thrombolytics such as heparin have been proposed in the literature.

Stents generally are coated by simple dip or spray coating of the stent with polymer or polymer and a pharmaceutical/therapeutic agent or drug. These methods were acceptable for early stent designs that were of open construction fabricated from wires (Wiktor stent) or from ribbons (Gianturco). Dip coating with relatively low coating weights (about 4% polymer) could successfully coat such stents without any problems such as excess coating bridging (i.e. forming a film across) the open space between structural members of the device. This bridging is of particular concern when coating more modern stents that are of less open construction, such as the Palmaz-Schatz, Crown, Multilink or GFX stents. Bridging of the open space (slots) is undesirable because it can interfere with the mechanical performance of the stent, such as expansion during deployment in a vessel lumen. Bridges may rupture upon expansion and provide sites that activate platelet deposition by creating flow disturbances in the adjacent hemodynamic environment or pieces of the bridging film may break off and cause further complications. Bridging of the open slots may also prevent endothelial cell migration complicating the endothelial cell encapsulation of the stent.

Similarly, spray coating can be problematic in that there is a significant amount of spray lost during the process and many of the pharmaceutical agents that one would like to incorporate in the device are quite costly. In addition, in some cases it would be desirable to provide coated stents with high levels of coating and drug. High concentration coatings (~15% polymer with additional drug) are the preferred means to achieve high drug loading. Multiple dip-coating has been described in the literature as a means to build thicker coatings on the stent. However, composition and phase dispersion of the pharmaceutical agents affect sustained release profile of the pharmaceutical agent. In addition, the application of multiple dip coats from low concentration solutions often has the effect of reaching a limiting loading level as an equilibrium is reached between the solution concentration and the amount of coating, with or without pharmaceutical agent, deposited on the stent. Thus there is a continuing need for new and improved stent coating techniques.

At a thermodynamic state above the critical temperature and pressure, gases can exist as fluids which exhibit a number of unique properties. Supercritical fluids (SCF's) are dense gases and liquids at conditions above their respective thermodynamic critical points. By operating in the critical region, pressure and temperature can be used to regulate density, thus regulating the solvent power of SCF's. SCF's exhibit high solvent power for many normally insoluble substances and as such have been used for industrial applications such as the extraction of specific substances from liquid and solid mixtures. For example, SCF's have been used for decaffeination of coffee, removal of saturated fats and cholesterol from snacks and food products and other extraction processes, and to test the presence of pesticides in crops.

In addition to their use in extraction processes, SCF's have recently been proposed for use in the deposition of thin films. U.S. Pat. No. 4,737,384 to Murthy et al. describes a process for depositing a thin metal or polymer coating on a substrate by exposing the substrate at supercritical temperatures and pressures to a solution containing the metal or polymer in a solvent and reducing the pressure or temperature to subcritical values to deposit a thin coating of the metal or polymer on the substrate. PCT application WO 99/19085 describes a method of preparing coatings of thin films onto particulate substances using SCF's. Neither of these references however, disclose the use of SCF's for the coating of stents or other medical devices.

SUMMARY OF THE INVENTION

The invention relates to a process for coating stents and other medical devices with a thin film polymer optionally containing a therapeutic agent, using a supercritical fluid deposition process. The process comprises the steps of:

(1) contacting the stent or other medical device with a liquid coating solution comprising a film forming biocompatible polymer and an optional therapeutic agent in a solvent under super critical temperature and pressure conditions such that the polymer and therapeutic agent are solubilized under the super critical conditions but insoluble under sub-critical conditions; and (2) reducing the pressure and/or temperature conditions to sub-critical levels to deposit a thin film coating of said polymer and optional therapeutic agent on the stent or other medical device.

In another embodiment, the stent or other medical device is coated using super critical fluid as an anti-solvent. In this process, the polymer and optional drug combination is dissolved in suitable solvent and exposed to the stent or other medical device. The super critical fluid is then used to extract the solvent, thereby depositing a thin film of the polymer and optional drug on the surface of the stent or other medical device.

In still another embodiment of the invention, the stent or other medical device is coated with a drug and polymer by using a combination GAS/RESS procedure. This process comprises the steps of:

(a) contacting the stent or other medical device with a drug dissolved in a suitable solvent;

(b) removing the solvent by extracting the solvent under sub-critical or super critical conditions using a super critical fluid as an anti-solvent to dissolve the solvent from the drug solution, thus precipitating the drug on the surface of the stent or other medical device;

(c) contacting the stent or other medical device with a liquid coating solution comprising a film forming biocompatible polymer in a solvent under super critical temperature and pressure conditions such that the polymer is solubilized under the super critical conditions but insoluble under sub-critical conditions; and (d) reducing the pressure and/or temperature conditions to sub-critical levels to deposit a thin film coating of said polymer on the stent or other medical device.

In another embodiment of the invention there is provided a stent or other medical device coated with a film forming biocompatible polymer and an optional therapeutic agent wherein the polymer and optional therapeutic agent are deposited on the stent or medical device using a super critical fluid nucleation process. The process of the invention provides a coated stent with an exceptionally smooth surface which is advantageous in preventing restenosis.

Through application of the preferred combination GAS/RESS procedure of the invention, the process yields a drug+polymer coated stent that has the potential advantage of minimizing the burst release of the drug since the process involves first coating the drug and then putting the polymer coat on top of it.

Several advantages resulting from the process of this invention are compared to conventional polymer dipping processes. For example, the process is environmentally friendly and does not require the use of toxic solvents and the process is fully contained so there is no exposure of the drugs to production personnel and the environment. The process can employ relatively inexpensive substances such as carbon dioxide which can be recycled.

DETAILED DESCRIPTION

Figure 1:
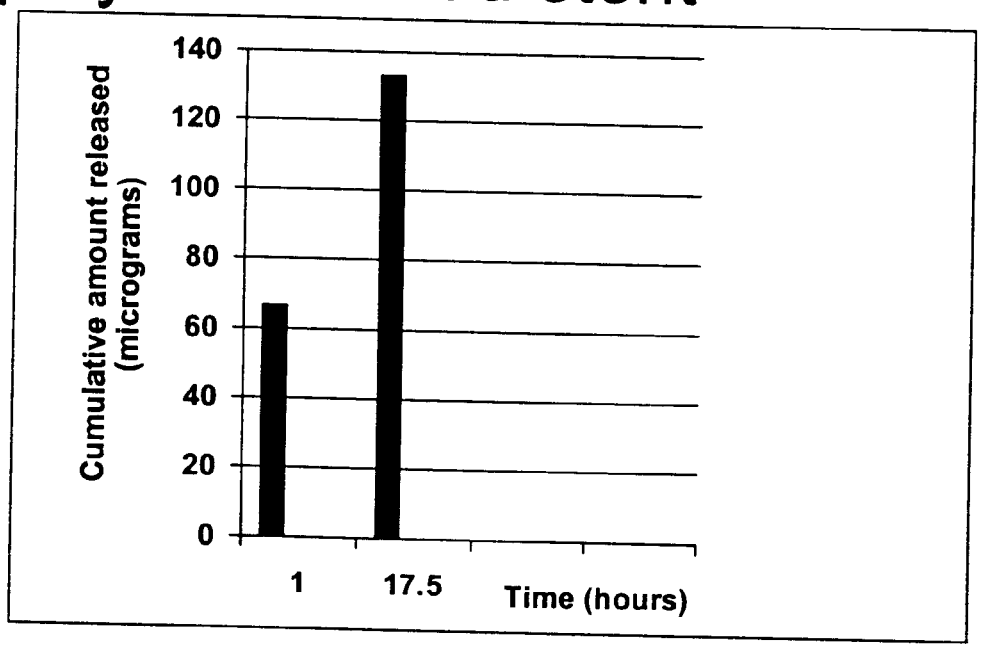
FIG. 1 is a graph showing the cumulative release of RWJ-53308 thrombolytic agent from a polymer coated stent.

The present invention provides a process for coating stents and other medical devices using super critical fluid deposition. In accordance with the invention, the stent or other medical device to be coated is exposed to a solution of a film forming biocompatible polymer and or optional therapeutic agent in suitable solvent under super critical conditions. A suitable solvent is one in which the polymer and optional therapeutic agent is not soluble under sub-critical conditions, but is soluble under super critical conditions. In practicing the process of the present invention, the stent or device, the coating material and the optional therapeutic agent can be placed in a suitable chamber such as an autoclave which is then filled with a supercritical fluid under conditions of temperature and pressure required to dissolve the coating material. When the temperature and/or pressure conditions are lowered to sub-critical conditions, the polymer and optional therapeutic agent are deposited as a thin film on the surface of the stent or medical device.

Alternatively, a solvent in which the polymer and therapeutic agent is soluble under normal conditions may be employed and the solvent is extracted using a super critical fluid, thereby depositing the polymer and therapeutic agent on the surface of the stent or other medical device.

Coating Materials

Film-forming polymers that can be used for coatings in this application can be absorbable or non-absorbable and must be biocompatible to minimize irritation to the vessel wall. The polymer may be either biostable or bioabsorbable depending on the desired rate of release or the desired degree of polymer stability, but a bioabsorbable polymer is preferred since, unlike biostable polymer, it will not be present long after implantation to cause any adverse, chronic local response. Furthermore, bioabsorbable polymers do not present the risk that over extended periods of time there could be an adhesion loss between the stent and coating caused by the stresses of the biological environment that could dislodge the coating and introduce further problems even after the stent is encapsulated in tissue.

Suitable film-forming bioabsorbable polymers that could be used include polymers selected from the group consisting of aliphatic polyesters, poly(amino acids), copoly(ether-esters), polyalkylenes oxalates, polyamides, poly(iminocarbonates), polyorthoesters, polyoxaesters, polyamidoesters, polyoxaesters containing amido groups, poly(anhydrides), polyphosphazenes, biomolecules and blends thereof. For the purpose of this invention aliphatic polyesters include homopolymers and copolymers of lactide (which includes lactic acid d-, l- and meso lactide), $\epsilon$-caprolactone, glycolide (including glycolic acid), hydroxybutyrate, hydroxyvalerate, para-dioxanone, trimethylene carbonate (and its alkyl derivatives), 1,4-dioxepan-2-one, 1,5-dioxepan-2-one, 6,6-dimethyl-1,4-dioxan-2-one and polymer blends thereof. Poly(iminocarbonate) for the purpose of this invention include those described by Kemnitzer and Kohn, in the *Handbook of Biodegradable Polymers*, edited by Domb, Kost and Wisemen, Hardwood Academic Press, 1997, pages 251–272. Copoly(ether-esters) for the purpose of this invention include those copolyester-ethers described in Journal of Biomaterials Research, Vol. 22, pages 993–1009, 1988 by Cohn and Younes and Cohn, Polymer Preprints (ACS Division of Polymer Chemistry) Vol. 30(1), page 498, 1989 (e.g. PEO/PLA). Polyalkylene oxalates for the purpose of this invention include U.S. Pat. Nos. 4,208,511; 4,141,087; 4,130,639; 4,140,678; 4,105,034; and 4,205,399 (incorporated by reference herein). Polyphosphazenes, co-, ter- and higher order mixed monomer based polymers made from L-lactide, D,L-lactide, lactic acid, glycolide, glycolic acid, para-dioxanone, trimethylene carbonate and $\epsilon$-caprolactone such as are described by Allcock in *The Encyclopedia of Polymer Science*, Vol. 13, pages 31–41, Wiley Intersciences, John Wiley & Sons, 1988 and by Vandorpe, Schacht, Dejardin and Lemmouchi in the *Handbook of Biodegradable Polymers*, edited by Domb, Kost and Wisemen, Hardwood Academic Press, 1997, pages 161–182 (which are hereby incorporated by reference herein). Polyanhydrides from diacids of the form HOOC—$C_6H_4$—O—$(CH_2)_m$—O—$C_6H_4$—COOH where m is an integer in the range of from 2 to 8 and copolymers thereof with aliphatic alpha-omega diacids of up to 12 carbons. Polyoxaesters, polyoxaamides and polyoxaesters containing amines and/or amido groups are described in one or more of the following U.S. Pat. Nos. 5,464,929; 5,595,751; 5,597, 579; 5,607,687; 5,618,552; 5,620,698; 5,645,850; 5,648,088; 5,698,213 and 5,700,583; (which are incorporated herein by reference). Polyorthoesters such as those described by Heller in *Handbook of Biodegradable Polymers*, edited by Domb, Kost and Wisemen, Hardwood Academic Press, 1997, pages 99–118 (hereby incorporated herein by reference). Film-forming polymeric biomolecules for the purpose of this invention include naturally occurring materials that may be enzymatically degraded in the human body or are hydrolytically unstable in the human body such as fibrin, fibrinogen, collagen, elastin, and absorbable biocompatable polysaccharides such as chitosan, starch, fatty acids (and esters thereof), glucoso-glycans and hyaluronic acid.

Suitable film-forming biostable polymers with relatively low chronic tissue response, such as polyurethanes, silicones, poly(meth)acrylates, polyesters, as well as, hydrogels such as those formed from polyvinyl pyrrolidinone and polyesters could also be used. Other polymers could also be used if they can be dissolved, cured or polymerized on the stent. These include polyolefins, polyisobutylene and ethylene-alphaolefin copolymers; acrylic polymers and copolymers, vinyl halide polymers and copolymers, such as polyvinyl chloride; polyvinyl ethers, such as polyvinyl methyl ether; polyvinylidene halides such as polyvinylidene fluoride and polyvinylidene chloride; polyacrylonitrile, polyvinyl ketones; polyvinyl aromatics such as polystyrene; polyvinyl esters such as polyvinyl acetate; copolymers of vinyl monomers with each other and olefins, such as etheylene-methyl methacrylate copolymers, acrylonitrile-styrene copolymers, ABS resins and ethylene-vinyl acetate copolymers; polyamides, such as Nylon 66 and polycaprolactam; alkyd resins; polycarbonates; polyoxymethylenes; polyimides; polyethers; epoxy resins, polyurethanes; rayon; rayon-triacetate, cellulose, cellulose acetate, cellulose acetate butyrate; cellophane; cellulose nitrate; cellulose propionate; cellulose ethers; and carboxymethyl cellulose. Polyamides for the purpose of this application would also include polyamides of the form —NH—$(CH_2)_n$—CO— and NH—$(CH_2)_x$—NH—CO—$(CH_2)_y$—CO, wherein n is preferably an integer in from 6 to 13; x is an integer in the range of form 6 to 12; and y is an integer in the range of from 4 to 16. The list provided above is illustrative but not limiting.

The polymers used for coatings must be film-forming polymers that have molecular weight high enough as to not be waxy or tacky. The polymers also must adhere to the stent and not be so readily deformable after deposition on the stent as to be able to be displaced by hemodynamic stresses. The polymers molecular weight should be high enough to provide sufficient toughness so that the polymers will not to be rubbed off during handling or deployment of the stent and must not crack during expansion of the stent. The melting point of the polymer used in the present invention should have a melting temperature above about 40° C., preferably above about 45° C., more preferably above about 50° C. and most preferably above about 55° C.

The preferable coatings to use for this application are bioabsorbable elastomers, more preferably aliphatic polyester elastomers. In the proper proportions aliphatic polyester copolymers are elastomers. Elastomers present the advantage that they tend to adhere well to the metal stents and can withstand significant deformation without cracking. The high elongation and good adhesion provide superior performance to other polymer coatings when the coated stent is expanded. Examples of suitable bioabsorbable elastomers are described in U.S. Pat. No. 5,468,253 hereby incorporated by reference. Preferably the bioabsorbable biocompatible elastomers based on aliphatic polyester, including but not limited to those selected from the group consisting of elastomeric copolymers of $\epsilon$-caprolactone and glycolide (preferably having a mole ratio of $\epsilon$-caprolactone to glycolide of from about 35:65 to about 65:35, more preferably from about 45:55 to about 35:65) elastomeric copolymers of $\epsilon$-caprolactone and lactide, including L-lactide, D-lactide blends thereof or lactic acid copolymers (preferably having a mole ratio of $\epsilon$-caprolactone to lactide of from about 35:65 to about 90:10 and more preferably from about 35:65 to about 65:35 and most preferably from about 45:55 to about 30:70 or from about 90:10 to about 80:20) elastomeric copolymers of p-dioxanone (1,4-dioxan-2-one) and lactide including L-lactide, D-lactide and lactic acid (preferably having a mole ratio of p-dioxanone to lactide of from about 40:60 to about 60:40) elastomeric copolymers of $\epsilon$-caprolactone and p-dioxanone (preferably having a mole ratio of $\epsilon$-caprolactone to p-dioxanone of from about 30:70 to about 70:30) elastomeric copolymers of p-dioxanone and trimethylene carbonate (preferably having a mole ratio of p-dioxanone to trimethylene carbonate of from about 30:70 to about 70:30), elastomeric copolymers of trimethylene carbonate and glycolide (preferably having a mole ratio of trimethylene carbonate to glycolide of from about 30:70 to about 70:30), elastomeric copolymer of trimethylene carbonate and lactide including L-lactide, D-lactide, blends thereof or lactic acid copolymers (preferably having a mole ratio of trimethylene carbonate to lactide of from about 30:70 to about 70:30) and blends thereof. As is well known in the art these aliphatic polyester copolymers have different hydrolysis rates, therefore, the choice of elastomer may in part be based on the requirements for the coating's adsorption. For example $\epsilon$-caprolactone-co-glycolide copolymer (45:55 mole percent, respectively) films lose 90% of their initial strength after 2 weeks in simulated physiological buffer whereas the $\epsilon$-caprolactone-co-lactide copolymers (40:60 mole percent, respectively) loses all of its strength between 12 and 16 weeks in the same buffer. Mixtures of the fast hydrolyzing and slow hydrolyzing polymers can be used to adjust the time of strength retention.

The preferred bioabsorbable elastomeric polymers should have an inherent viscosity of from about 1.0 dL/g to about 4 dL/g, preferably an inherent viscosity of from about 1.0 dL/g to about 2 dL/g and most preferably an inherent viscosity of from about 1.2 dL/g to about 2 dL/g as determined at about 25° C. in a 0.1 gram per deciliter (g/dL) solution of polymer in hexafluoroisopropanol (HFIP).

In the case of stents, the film-forming biocompatible polymer coatings are generally applied to reduce turbulence in blood flow through the stent, as well as, adverse tissue reactions. The coating may also be used to administer a pharmaceutically active material to the site of the stent's placement. Generally, the amount of polymer coating to be placed on the stent will vary with the polymer and the stent design and the desired effect of the coating. As a guideline the amount of coating may range from about 0.5 to about 20 as a percent of the total weight of the stent after coating and preferably will range from about 1 to about 15 percent. The polymer coatings may be applied in one or more coating steps depending on the amount of polymer to be applied. Different polymers may also be used for different layers in the stent coating. In fact it is highly advantageous to use a dilute first coating solution as primer to promote adhesion of a subsequent coating layer that may contain pharmaceutically active materials.

Super Critical Fluids

The preferred supercritical fluid is super critical carbon dioxide ($SCCO_2$). $CO_2$ has been attractive for SCF use because it is cheap, nonflammable, nontoxic and readily available. In the case of SCCO$_2$, typical initial operating condition will be approximately 31 to 80° C. and pressures of 70 to 25 bars, although higher values of either or both parameters may be used, provided of course, that the higher values do not have a deleterious effect on the substrate being coated or the therapeutic agent, if employed. With SCF systems other than CO$_2$, suitable operating temperatures and pressures will be at least the minimum necessary to form a super critical fluid with such systems. The following table specifies the conditions for a number of materials commonly used as SCF's.

TABLE 1

| Solvents | $T_c$ (° C.) | $P_c$ (bar) |
|---|---|---|
| CO$_2$ | 31.1 | 73.8 |
| Ethane | 32.2 | 48.8 |
| Water | 374.2 | 220.5 |
| Ammonia | 132.5 | 112.8 |
| Isopropanol | 235.2 | 47.6 |

In any case, the selection of the solvent to be used as the SCF will depend on the coating substance being deposited and the therapeutic agent employed, if any. In general, the SCF used will be one in which the material is substantially soluble at or above the critical temperature and pressure of the solvent and substantially insoluble in the solvent at some subcritical temperature and pressure. The SCF may or may not contain an entrainer; i.e. a substance added to the SCF system in small amounts in order to enhance the solubility of the substance in the SCF system. Suitable entrainers include but are not limited to ketones, alcohols, esters and chlorinated solvents.

The SCF solvent is chosen such that there is the proper balance of viscosity, deposition level of the polymer, solubility of the pharmaceutical agent in the SCF solvent, wetting of the stent and nucleation and removal rate of the solvent to properly coat the stents. In the preferred embodiment, the solvent is chosen such that the therapeutic agent and the polymer are both soluble in the solvent. In some cases, the solvent must be chosen such that the coating polymer is soluble in the solvent and the pharmaceutical agent is dispersed in the polymer solution in the solvent. In that case the solvent chosen must be able to suspend small particles of the pharmaceutical agent without causing them to aggregate or agglomerate into collections of particles that would clog the slots of the stent when applied. Although the goal is to dry the solvent completely from the coating during processing, it is a great advantage for the solvent to be non-toxic, non-carcinogenic and environmentally benign. Mixed solvent systems can also be used to control viscosity and nucleation rates. In all cases, the solvent must not react with or inactivate the pharmaceutical agent or react with the coating polymer.

Substances to be Coated

In the preferred embodiment, the substance to be coated is a stent. Stents are generally cylindrical structures perforated with passages that are slots, ovoid, circular or the like shape. Stents may also be composed of helically wound or serpentine wire structures in which the spaces between the wires form the passages. Stents may be flat perforated structures that are subsequently rolled to form tubular structures or cylindrical structures that are woven, wrapped, drilled, etched or cut to form passages. Examples of stents that may be advantageously coated by the present process include but are not limited stents described in the following U.S. Pat. Nos. 4,733,665; 4,800,882 (hereinafter the Gianturco stent); U.S. Pat. No. 4,886,062 (hereinafter the Wiktor stent) and U.S. Pat. No. 5,514,154 (hereinafter the Guidant RX Multilink™ stent. These stents can be made of biocompatible materials including biostable and bioabsorbable materials. Suitable biocompatible metals include, but are not limited to, stainless steel, tantalum, titanium alloys (including nitinol), and cobalt alloys (including cobalt-chromium-nickel alloys). Suitable nonmetallic biocompatible materials include, but are not limited to, polyamides, polyolefins (i.e. polypropylene, polyethylene etc.), nonabsorbable polyesters (i.e. polyethylene terephthalate), and bioabsorbable aliphatic polyesters (i.e. homopolymers and copolymers of lactic acid, glycolic acid, lactide, glycolide, para-dioxanone, trimethylene carbonate, $\epsilon$-caprolactone, etc. and blends thereof).

Other medical devices which may be coated utilizing the process of the invention include cathethers, forceps, hypodermic needles, blades, scissors, Jacobson titanium needle holders, Jones I.M.A. diamond knife, epicardial retractors, and the like.

Therapeutic Agents

The coatings can be used to deliver therapeutic and pharmaceutic agents such as, but not limited to: antiproliferative/antimitotic agents including natural products such as vinca alkaloids (i.e. vinblastine, vincristine, and vinorelbine), paclitaxel, epidipodophyllotoxins (i.e. etoposide, teniposide), antibiotics (dactinomycin (actinomycin D) daunorubicin, doxorubicin and idarubicin), anthracyclines, mitoxantrone, bleomycins, plicamycin (mithramycin) and mitomycin, enzymes (L-asparaginase which systemically metabolizes L-asparagine and deprives cells which don't have the capacity to synthesize their own asparagine); antiproliferative/antimitotic alkylating agents such as nitrogen mustards(mechlorethamine, cyclophosphamide and analogs, melphalan, chlorambucil), ethylenimines and methylmelamines (hexamethylmelamine and thiotepa), alkyl sulfonates-busulfan, nirosoureas (carmustine (BCNU) and analogs, streptozocin), trazenes—dacarbazinine (DTIC); antiproliferative/antimitotic antimetabolites such as folic acid analogs (methotrexate), pyrimidine analogs (fluorouracil, floxuridine, and cytarabine), purine analogs and related inhibitors (mercaptopurine, thioguanine, pentostatin and 2-chlorodeoxyadenosine{cladribine}); platinum coordination complexes (cisplatin, carboplatin), procarbazine, hydroxyurea, mitotane, aminoglutethimide; hormones (i.e. estrogen); Anticoagulants (heparin, synthetic heparin salts and other inhibitors of thrombin); fibrinolytic agents (such as tissue plasminogen activator, streptokinase and urokinase); antiplatelet:(aspirin, dipyridamole, ticlopidine, clopidogrel, abciximab); antimigratory; antisecretory (breveldin); antiinflammatory: such as adrenocortical steroids (cortisol, cortisone, fludrocortisone, prednisone, prednisolone, 6$\alpha$-methylprednisolone, triamcinolone, betamethasone, and dexamethasone), non-steroidal agents (salicylic acid derivatives i.e. aspirin; para-aminophenol derivatives i.e. acetominophen; Indole and indene acetic acids (indomethacin, sulindac, and etodalac), heteroaryl acetic acids (tolmetin, diclofenac, and ketorolac), arylpropionic acids (ibuprofen and derivatives), anthranilic acids (mefenamic acid, and meclofenamic acid), enolic acids (piroxicam, tenoxicam, phenylbutazone, and oxyphenthatrazone), nabumetone, gold compounds (auranofin, aurothioglucose, gold sodium thiomalate); immunosuppressive: (cyclosporine, tacrolimus (FK-506), sirolimus (rapamycin), azathioprine, mycophenolate mofetil); Angiogenic: vascular endothelial growth factor (VEGF), fibroblast growth factor (FGF); nitric oxide donors; anti-sense oligo nucleotides and combinations thereof.

In one embodiment of the invention, the therapeutic agent used in the stent coating is the compound known as elarofiban (3-Pyridinepropanoic acid, b-[[[(3R)-1-[1-oxo-3-(4-piperidinyl)propyl]-3-piperidinyl]carbonyl]amino]-, (bS)-(9CI), RWJ-53308), an anti-thrombolytic agent under development which is disclosed in patent application U.S. Ser. No. 08/841,016 filed Apr. 29, 1997, hereby incorporated by reference.

Coating with the therapeutic agent may be formulated by mixing one or more therapeutic agents with the coating polymers in a coating mixture. The therapeutic agent may be present as a liquid, a finely divided solid, or any other appropriate physical form. Optionally, the mixture may include one or more additives, e.g., nontoxic auxiliary substances such as diluents, carriers, excipients, stabilizers or the like. Other suitable additives may be formulated with the polymer and pharmaceutically active agent or compound. For example hydrophilic polymers selected from the previously described lists of biocompatible film forming polymers may be added to a biocompatible hydrophobic coating to modify the release profile (or a hydrophobic polymer may be added to a hydrophilic coating to modify the release profile). One example would be adding a hydrophilic polymer selected from the group consisting of polyethylene oxide, polyvinyl pyrrolidone, polyethylene glycol, carboxylmethyl cellulose, hydroxymethyl cellulose and combination thereof to an aliphatic polyester coating to modify the release profile. Appropriate relative amounts can be determined by monitoring the in vitro an/or in vivo release profiles for the therapeutic agents.

The best conditions for the coating application are when the polymer and pharmaceutic agent have a common solvent. This provides a wet coating that is a true solution. Less desirable, yet still usable are coatings that contain the pharmaceutic as a solid dispersion in a solution of the polymer in solvent. Under the dispersion conditions, care must be taken to ensure that the particle size of the dispersed pharmaceutical powder, both the primary powder size and its aggregates and agglomerates, is small enough not to cause an irregular coating surface or to clog the slots of the stent that need to be kept coating-free. That is why Tween® 80 which is a surfactant and can also act as a plasticizer is generally employed in the coating solution. This gives flexibility to the polymer and if the drug is hydrophobic, the surfactant nature will prevent aggregation.

The amount of therapeutic agent will be dependent upon the particular drug employed and medical condition being treated. Typically, the amount of drug represents about 0.001% to about 70%, more typically about 0.001% to about 60%, most typically about 0.001% to about 45% by weight of the coating. The quantity and type of polymers employed in the coating layer containing the pharmaceutic agent will vary depending on the release profile desired and the amount of drug employed. The product may contain blends of the same or different polymers having different molecular weights to provide the desired release profile or consistency to a given formulation.

Absorbable polymers, upon contact with body fluids including blood or the like, undergo gradual degradation (mainly through hydrolysis) with concomitant release of the dispersed drug for a sustained or extended period (as compared to the release from an isotonic saline solution). Non-absorbable and absorbable polymers may release dispersed drug by diffusion. This can result in prolonged delivery (over approximately 1 to 2,000 hours, preferably 2 to 800 hours) of effective amounts (approximately 0.001 $\mu$g/cm$^2$-min to 100 $\mu$g/cm$^2$-min) of the drug. The dosage can be tailored to the subject being treated, the severity of the affliction, the judgment of the prescribing physician, and the like.

Individual formulations of drugs and polymers may be tested in appropriate in vitro and in vivo models to achieve the desired drug release profiles. For example, a drug could be formulated with a polymer (or blend) coated on a stent and placed in an agitated or circulating fluid system (such as PBS 4% bovine albumin). Samples of the circulating fluid could be taken to determine the release profile (such as by HPLC). The release of a pharmaceutical compound from a stent coating into the interior wall of a lumen could be modeled in an appropriate porcine system. The drug release profile could then be monitored by appropriate means such as, by taking samples at specific times and assaying the samples for drug concentration (using HPLC to detect drug concentration). Thrombus formation can be modeled in animal models using the $^{111}$ In-platelet imaging methods described by Hanson and Harker, Proc. Natl. Acad. Sci. USA 85:3184–3188 (1988). Following this or similar procedures, those skilled in the art will be able to formulate a variety of stent coating formulations.

General Description of the Process of the Invention

Deposition of a coating by the process disclosed herein involves altering the temperature and pressure of an SCF in which the desired coating material is dissolved. In one embodiment of the present invention, a stent is placed in a chamber such as an autoclave or other pressurizable container with the coating materials. The chamber is constructed such that super critical conditions can be achieved. The chamber is pressurized and the SCF solvent is introduced in the chamber. The chamber is then brought to super critical conditions by changing temperature and/or pressure inside the chamber, and the coating material becomes suspended in the SCF. The conditions are maintained for sufficient time to allow for equilibration, (e.g. 1 hour) and the system is then restored to sub-critical conditions resulting in precipitation of the coating material on the stent surface.

Preferably, the temperature and/or pressure in the chamber is restored to sub-critical conditions in a controlled manner so that the deposition of the coating material can be controlled.

Figure 2:
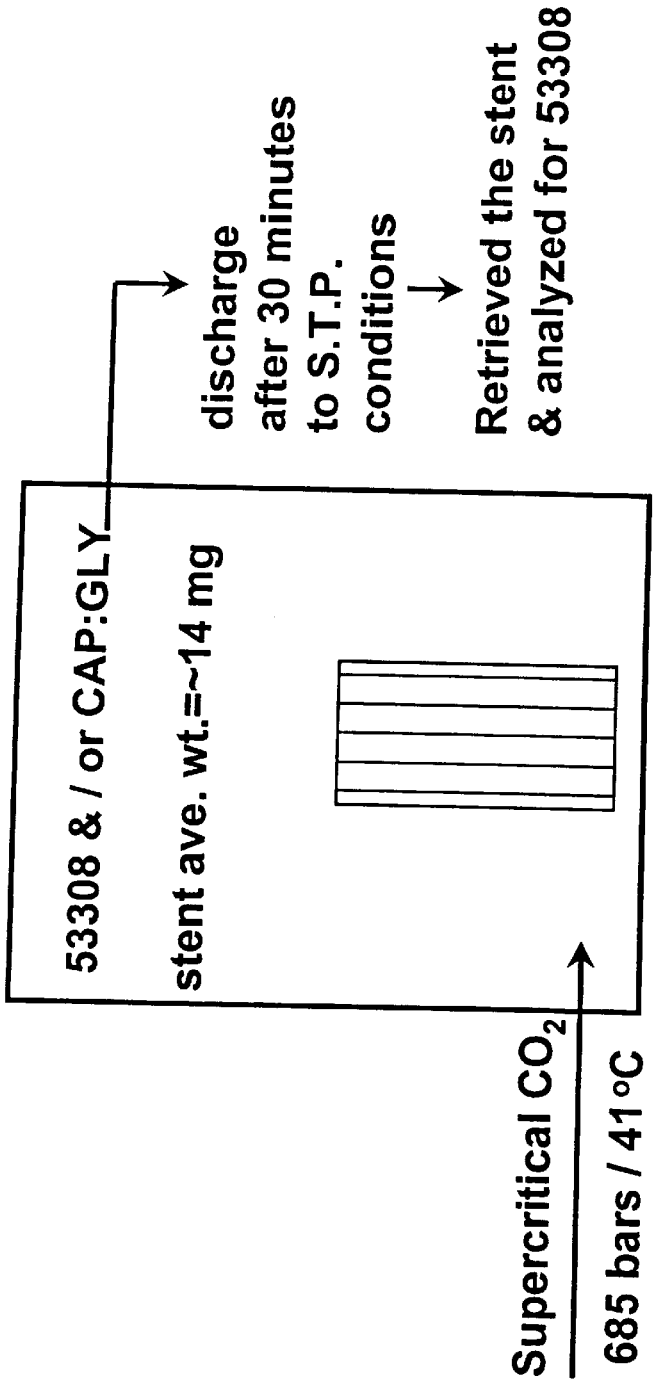
FIG. 2 is a diagram illustrating the GAS/RESS procedure for coating a stent according to the invention.

In the preferred embodiment a Gas Anti-Solvent (GAS)—Rapid Expansion of Super-critical Solution (RESS) combination process is used to coat drug and polymers on the stent as illustrated in FIG. 2. In the first step the drug is coated on the stent surface by the GAS process and then the drug coated stent is coated with the polymer by the RESS process. In this procedure the substrate for the polymer coating is not just a metal surface. It is a metal surface of a stent coated with a drug. Such an approach is advantageous from the drug release point of view. Having the drug under the polymer coat reduces the initial burst effect of the drug thereby reducing the immediate release of drug from the stent (device) once the coated device comes in contact with a biological medium.

Thus, in this embodiment of the invention there is provided a stent or other medical device coated with a drug by contacting the stent with a drug solution and coating by using the super-critical fluid as an antisolvent. In this process the SCF dissolves the solvent from the drug solution thus precipitating the drug on the surface of the stent. This process can take place under sub or supercritical conditions. This is the GAS process. This coated stent is then subjected to the RESS process where the polymer is dissolved in the SCF under sub or supercritical conditions. Once the polymer is in solution, the pressure and/or temperature are reduced to standard temperature and pressure conditions thereby precipitating the polymer on the drug coated surface of the stent or other medical/surgical device.

The following examples are intended to illustrate but not to limit the invention.

EXAMPLE 1

Rapid Expansion (RESS) Coating Method of Stent

| Polymer: | PLGA Poly lactide-co-glycolide (Poly lactide-co-glycolic acid) |
|---|---|
| No Drug | |
| Pressure: | 100,000 psi |
| Temperature: | 40 degrees C. |

Figure 3:
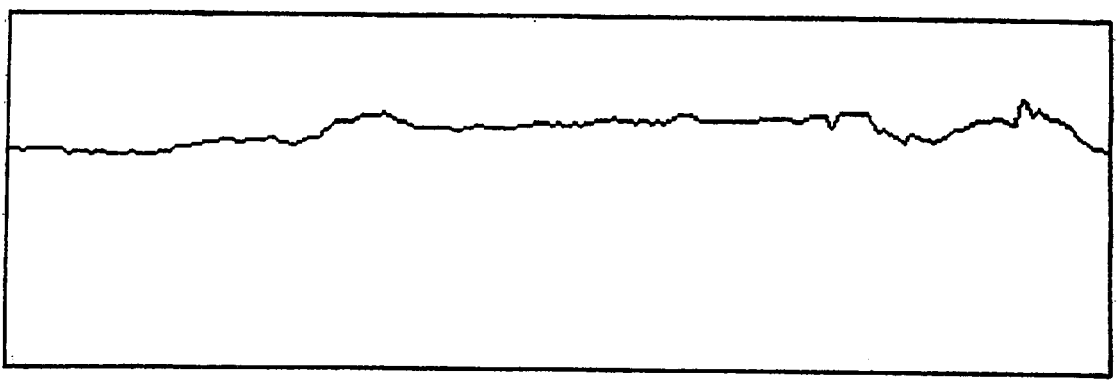
FIG. 3 is non-contact surface profilometer scan of the the outside surface of a coated stent.
Figure 4:
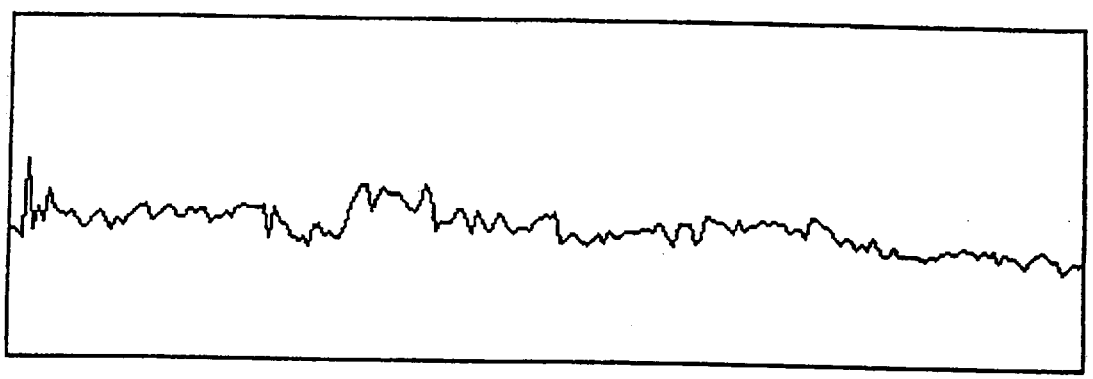
FIG. 4 is non-contact surface profilometer scan of the the inside surface of a coated stent.
Figure 5:
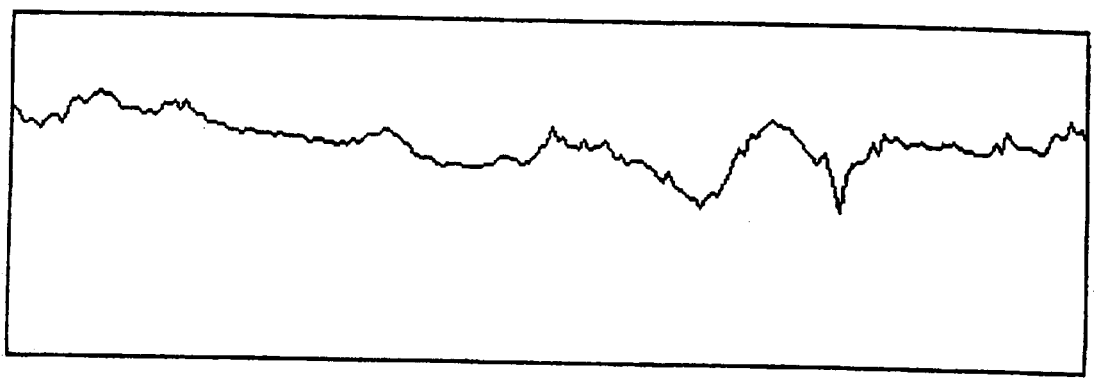
FIG. 5 is non-contact surface profilometer scan of the the outside surface of an uncoated stent.
Figure 6:
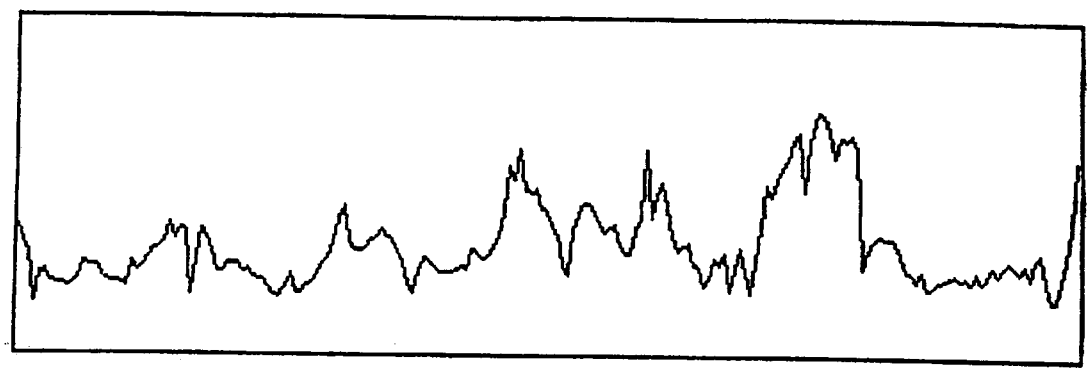
FIG. 6 is non-contact surface profilometer scan of the the inside surface of an uncoated stent.

The vial containing the stent was placed in the reaction vessel with PLGA. The temperature adjusted to 40 degrees and the pressure increased to 10,000 psi. After about 30 minutes the vessel was rapidly depressurized and the stent was retrieved from the vial. This coated stent was observed for surface roughness using the Horizon 200 non-contact surface profilometer by Burleigh, Burleigh Park, Fischers, N.Y. 14453-0755. The surface scans are attached hereto as FIGS. 3, 4, 5 and 6. FIGS. 3 and 4 are the outside and inside surface scan respectively, of the coated stent. FIGS. 5 and 6 are the outside and inside surface scan respectively, of the uncoated stent. The various parameters calculated from these scans are:

TABLE 2

| | $R_q$ (RMS roughness) μm | $R_a$ (average roughness) μm | $R_t$ (Peak to valley ratio) μm |
|---|---|---|---|
| Coated outside surface | 0.47 | 0.40 | 1.99 |
| Coated inside surface | 0.52 | 0.42 | 3.10 |
| Uncoated outside surface | 0.60 | 0.45 | 3.00 |
| Uncoated inside surface | 0.71 | 0.54 | 3.26 |

As seen from Table 2 above, the coated surfaces, both inside and outside, have corresponding lower RMS roughness, average roughness and peak to valley ratio values than the uncoated surfaces. This indicates that the polymer coated the stent surface both inside and outside and in the process reduced the surface roughness.

EXAMPLE 2

Gas Anti-Solvent (GASS) Stent Coating Method with Anti-Thrombolytic Agent

| RWJ-53308 | 1.64 mg |
|---|---|
| Tween ® 80 | 0.58 mg |
| (Stent | 15.9 mg) |
| Water | 20 uL | a. RWJ-53308 Deposition on Stent by the GASS Method:

This example demonstrates the coating of a stent with an anti-thrombolytic agent designated RWJ-53308, {elarofiban (3-Pyridinepropanoic acid, b-[[[(3R)-1-[1-oxo-3-(4-piperidinyl)propyl]-3-piperidinyl]carbonyl]amino]-, (bS)-(9CI))}, which is disclosed in patent application U.S. Ser. No. 08/841,016 filed Apr. 29, 1997, hereby incorporated by reference.

Dissolved the weighed quantity of RWJ-53308 in 20 ul water and 1.58 mg of Tween® 80 in a small conical centrifuge tube. Placed the stent in this tube. This tube was then placed in the pressure vessel. The temperature was adjusted to 40 degrees C. and the pressure was increased to 318 bars. The $CO_2$ flow rate was adjusted to 4.5–5 liters per minute. This dynamic mode was operational for 30 minutes. After 30 minutes the system was depressurized rapidly and the stent retrieved from the vessel.

b. Coating the RWJ-53308 Deposited Stent With PLGA by the RESS Method:

| PLGA | 1.95 mg |
|---|---|
| Stent weight | 15.5–15.7 mg |

The stent coated with RWJ-53308 obtained in step a above was placed in a container along with the weighed quantity of PLGA. The system temperature was adjusted to 40 degrees C. and the pressure was increased to 600 bar. The $CO_2$ flow rate was adjusted to 4.5–5 liters per minute. This dynamic mode was operational for 30 minutes. After 30 minutes the system was rapidly depressurized and the stent was retrieved from the vessel.

c. Determination of RWJ-53308 on the PLGA Coated Stent:

A coated stent obtained in step b above was placed in a tube with 2 mL. water. The coated stent was allowed to macerate for 24 hours. The aqueous supernatant was drained, filtered and UV absorbance was read at 261 nm. The amount of RWJ-53308 on the stent was calculated by comparing the absorbance value of a standard solution containing 147 μg/mL solution of RWJ-53308. Thus the supernatant obtained by extracting the drug from the PLGA coated stent contained 105 μg of RWJ-53308.

d. In-vitro Release Study of RWJ-53308 from PLGA Coated Stent:

A coated stent obtained in step b was placed in a tube with 2 mL of water. A 1 mL. aliquot was taken at the 1 hr and at the 17.5 hour time point. This 1 mL. aliquot was replaced with fresh water at each sampling. The sampled aliquot was analyzed by reading UV absorbance at 261 nm. The drug concentration was calculated by comparing the absorbance of a standard solution containing 147 μg/mL aqueous solution of RWJ-53308.

It was observed that approx. 66 ug of RWJ-53308 was released at 1 hour and a cumulative amount of approx. 134 ug was released at 17.5 hours as shown in FIG. 1.

We claim:

1. A process for coating stents and other medical devices with a thin film polymer optionally containing a therapeutic agent, using a supercritical fluid deposition process, comprising the steps of:
   (i) contacting the stent or other medical device with a liquid coating solution comprising a film forming biocompatible polymer and an optional therapeutic agent in a suitable solvent;
   (ii) extracting the solvent using a super critical anti-solvent under critical temperature and pressure conditions, thereby depositing a thin film of the polymer and optional drug on the surface of the stent or other medical device.

2. The process according to claim 1 wherein the super critical anti-solvent is selected from the group consisting of carbon dioxide, ethane, water, ammonia, and isopropanol.

3. The process according to claim 1 wherein the super critical anti-solvent is carbon dioxide.

4. A process for coating stents and other medical devices with a thin film polymer and a therapeutic agent, using a super-critical fluid deposition process, comprising the steps of:
   (i) contacting the stent or other medical device with a drug dissolved in a suitable solvent;
   (ii) extracting the solvent under super-critical conditions by dissolving the solvent from the drug solution using a super-critical anti-solvent thus precipitating the drug on the surface of the stent or other medical device;
   (iii) contacting the stent or other medical device with a liquid coating solution comprising a film forming biocompatible polymer in a solvent under super-critical temperature and pressure conditions such that the polymer is solubilized under the super-critical conditions but insoluble under sub-critical conditions; and
   (iv) reducing the pressure and/or temperature conditions to sub-critical levels to deposit a thin film coating of said polymer on the stent or other medical device.

5. The process according to claim 4 wherein the super critical solvent is selected from the group consisting of carbon dioxide, ethane, water, ammonia, and isopropanol.

6. The process according to claim 4 wherein the super critical solvent is carbon dioxide.

7. The process of claim 4 wherein the biocompatible coating material is selected from poly(lactide-co-glycolic acid), and $\epsilon$-caprolactone glycolic acid.

* * * * *